(12) United States Patent
Jakel et al.

(10) Patent No.: US 11,220,663 B2
(45) Date of Patent: Jan. 11, 2022

(54) SYSTEM AND PROCESS FOR CLARIFYING THIN STILLAGE

(71) Applicant: Fluid Quip Technologies, LLC, Springfield, OH (US)

(72) Inventors: Neal Jakel, Cedar Rapids, IA (US); John Kwik, Bellbrook, OH (US); Michael Franko, Denver, CO (US)

(73) Assignee: Fluid Quip Technologies, LLC, Springfield, OH (US)

( * ) Notice: Subject to any disclaimer, the term of this patent is extended or adjusted under 35 U.S.C. 154(b) by 0 days.

(21) Appl. No.: 15/299,964

(22) Filed: Oct. 21, 2016

(65) Prior Publication Data

US 2017/0114293 A1 Apr. 27, 2017

Related U.S. Application Data

(60) Provisional application No. 62/245,318, filed on Oct. 23, 2015.

(51) Int. Cl.
| | |
|---|---|
| *C12F 3/10* | (2006.01) |
| *B01D 21/01* | (2006.01) |
| *B01D 1/00* | (2006.01) |
| *B01D 21/24* | (2006.01) |
| *B01D 3/00* | (2006.01) |
| *C12P 7/06* | (2006.01) |

(52) U.S. Cl.
CPC .............. *C12F 3/10* (2013.01); *B01D 1/00* (2013.01); *B01D 3/002* (2013.01); *B01D 21/01* (2013.01); *B01D 21/2488* (2013.01); *C12P 7/06* (2013.01)

(58) Field of Classification Search
CPC ....................................................... C12F 3/10
See application file for complete search history.

(56) References Cited

U.S. PATENT DOCUMENTS

| | | | |
|---|---|---|---|
| 7,829,680 B1 | 11/2010 | Sander et al. | |
| 8,778,433 B2 | 7/2014 | Lee | |
| 9,012,191 B2 | 4/2015 | Lee | |
| 9,290,728 B2 | 3/2016 | Bootsma | |
| 2011/0230394 A1* | 9/2011 | Wiatr ..................... | A01N 31/02 514/2.4 |
| 2012/0064213 A1* | 3/2012 | Lee .......................... | B04B 3/04 426/472 |
| 2012/0245370 A1* | 9/2012 | Sheppard ................. | C11B 1/10 554/204 |
| 2012/0276593 A1* | 11/2012 | Li ............................ | C12P 7/06 435/95 |
| 2013/0236936 A1 | 9/2013 | Lee | |
| 2013/0309738 A1* | 11/2013 | Barr ......................... | C12P 7/16 435/160 |

(Continued)

OTHER PUBLICATIONS

Argentine Patent Office, Office Action issued in AR 20160103227 dated Oct. 7, 2020.

*Primary Examiner* — Peter Keyworth
(74) *Attorney, Agent, or Firm* — Wood Herron & Evans LLP (57) ABSTRACT

The present invention is directed to improved systems and processes for clarifying a thin stillage stream in a biofuel production process, such as a dry grind alcohol production process, that removes desirable amounts of insoluble solids from at least a portion of the thin stillage stream, thereby realizing any number of process enhancements.

20 Claims, 5 Drawing Sheets

(56) References Cited

U.S. PATENT DOCUMENTS

| | | | |
|---|---|---|---|
| 2014/0017728 A1* | 1/2014 | Bleyer | B01D 3/14 435/71.1 |
| 2014/0147897 A1 | 5/2014 | Lee | |
| 2016/0152931 A1 | 6/2016 | Bootsma | |

* cited by examiner

SYSTEM AND PROCESS FOR CLARIFYING THIN STILLAGE

TECHNICAL FIELD

The present invention relates generally to a system and process for use in the biofuel, biochemical, food, feed, nutrition, and/or pharmacy industries and, more specifically, to a system and process for clarifying at least a portion of a thin stillage stream in a biofuel production process, e.g., a dry grind alcohol production process.

BACKGROUND

Conventional processes for producing various types of biofuels, such as alcohol and other chemicals, from grains generally follow similar procedures. Wet mill processing plants convert, for example, corn grain into several different co-products, such as germ (for oil extraction), gluten feed (high fiber animal feed), gluten meal (high protein animal feed), and starch-based products such as alcohol (e.g., ethanol or butanol), high fructose corn syrup, or food and industrial starch. Dry grind plants generally convert grains, such as corn or fractions thereof, into two products, namely alcohol (e.g., ethanol or butanol) and distiller's grains with solubles. If sold as wet animal feed, distiller's wet grains with solubles are referred to as DWGS. If dried for animal feed, distiller's dried grains with solubles are referred to as DDGS. This co-product provides a secondary revenue stream that offsets a portion of the overall alcohol production cost.

Figure 1:
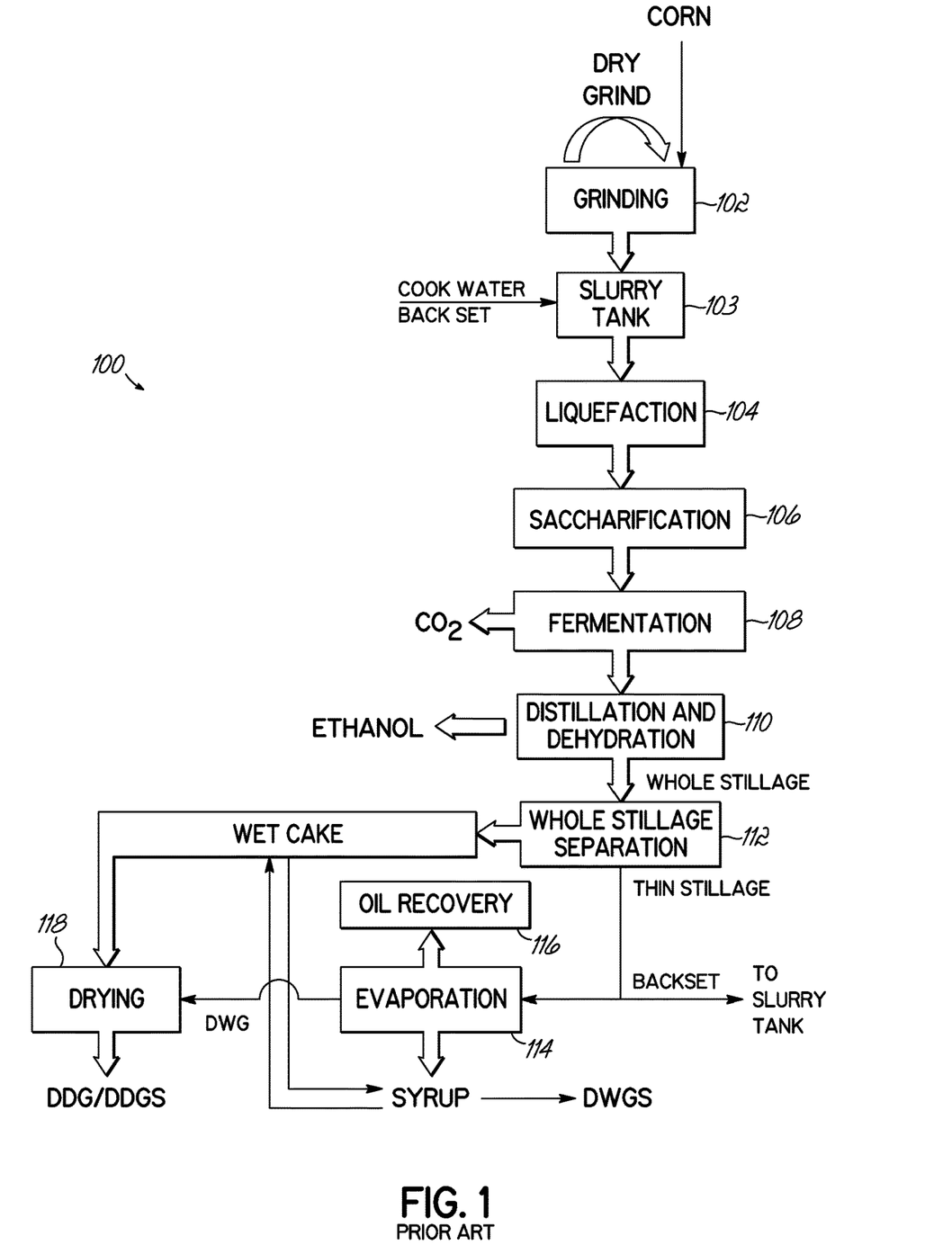
FIG. 1 is a flow diagram of a typical dry grind alcohol production process.

The overall yields for various co-products in the wet grind process can be less than desirable; and the wet grind process is complicated and costly, requiring high capital investment as well as high-energy and utility costs for operation. Because the capital cost of wet grind mills can be so prohibitive, some alcohol plants prefer to use the simpler dry grind process. FIG. 1 is a flow diagram of a typical dry grind alcohol (e.g., ethanol) production process 100. As a general reference point, the dry grind process 100 can be divided into a front end and a back end. The part of the process 100 that occurs prior to distillation 110 is considered the "front end", and the part of the process 100 that occurs after distillation 110 is considered the "back end". To that end, the front end of the dry grind process 100 begins with a grinding step 102 in which dried whole corn kernels can be passed through hammer mills for grinding into meal or a fine powder. The screen openings in the hammer mills or similar devices typically are of a size 5/64 to 9/64 inch, or about 1.98 mm to 3.57 mm, but some plants can operate at less than or greater than these screen sizes. The resulting particle distribution yields a very wide spread, bell type curve, which includes particle sizes as small as 45 micron and as large as 2 to 3 mm. The majority of the particles are in the range of 500 to 1200 micron, which is the "peak" of the bell curve.

After the grinding step 102, the ground meal is mixed with cook water (also referred to as backset) to create a slurry at slurry step 103, and a commercial enzyme called alpha-amylase is typically added (not shown). The slurry step 103 is followed by a liquefaction step 104 whereat the pH can be adjusted to about 5.2 to 5.8 and the temperature maintained between about 50° C. to 105° C. so as to convert the insoluble starch in the slurry to soluble starch. Various typical liquefaction processes occur at this liquefaction step 104, as is known in the art. The stream after the liquefaction step 104 has about 30% dry solids (DS) content, but can range from about 29-36%, with all the components contained in the corn kernels, including starch/sugars, protein, fiber, starch, germ, grit, and oil and salts, for example. Higher solids are achievable, but this requires extensive alpha amylase enzyme to rapidly breakdown the viscosity in the initial liquefaction step. There generally are several types of solids in the liquefaction stream: fiber, germ, and grit.

Liquefaction may be followed by separate saccharification and fermentation steps, 106 and 108, respectively, although in most commercial dry grind ethanol processes, saccharification and fermentation can occur simultaneously. This single step is referred to in the industry as "Simultaneous Saccharification and Fermentation" (SSF). Both saccharification and SSF can take as long as about 50 to 60 hours. Fermentation converts the sugar to alcohol. Yeast can optionally be recycled in a yeast recycling step (not shown) either during the fermentation process or at the very end of the fermentation process. Subsequent to the fermentation step 108 is the distillation (and dehydration) step 110, which utilizes a distillation to recover the alcohol. With distillation, alcohol is typically separated from the rest of the beer through a set of stepwise vaporizations and condensations. The beer less the alcohol separated through distillation is known as "whole stillage", which contains a slurry of the spent grains including corn protein, fiber, oil, and residual sugars/starches. These byproducts are too diluted to be of much value at this point and are further processed.

To that end, conventionally, the whole stillage from the distillation and dehydration step 110 is subjected to a whole stillage separation step 112 that can involve centrifuging the whole stillage to separate insoluble solids ("wet cake") from the liquid ("thin stillage"). In another example, the whole stillage may be conventionally separated using a dewatering decanter, such as a 2-stage dewatering decanter. The liquid, or thin stillage, from the whole stillage separation step 112 contains about 5% to 9% DS. The "wet cake" includes fiber at about 32% to 38% DS, of which there generally are three types: (1) pericarp, with average particle sizes typically about 1 mm to 3 mm; (2) tricap, with average particle sizes about 500 micron; (3) and fine fiber, with average particle sizes of about 250 micron. There may also be proteins with a particle size of about 45 to 300 micron.

Typically, the thin stillage stream is split at the back end to provide backset, which can be sent to the slurry tank 103 to help slurry the ground corn at the front end of the dry grind process (along with the cook water), with the other portion of the split feeding the evaporators to produce syrup. The split percentage can range from about a 20:80 ratio of evaporator feed to backset to about an 80:20 split. The remaining thin stillage portion of the split typically enters evaporators in an evaporation step 114 to boil or flash away moisture, leaving a thick syrup which contains the soluble (dissolved) solids (mainly protein and starches/sugars) from the fermentation (25 to 40% dry solids) along with residual oil and fine fiber. The concentrated slurry can be sent to a centrifuge to separate the oil from the syrup in an oil recovery step 116. The oil can be sold as a separate high value product. The oil yield is normally about 0.4 lb./bu of corn with high free fatty acids content. This oil yield recovers only about ¼ of the total oil in the corn kernel, with part of the oil passing with the syrup stream and the remainder being lost with the fiber/wet cake stream. About one-half of the oil inside the corn kernel remains inside the germ after the distillation step 110, which cannot be separated in the typical dry grind process using centrifuges. The free fatty acids content, which is created when the oil is heated and exposed to oxygen throughout the front and back-end process, reduces the value of the oil. The (de-oil)

centrifuge only removes less than 50% because the protein and oil make an emulsion, which cannot be satisfactorily separated.

The syrup, which has more than 10% oil, can be mixed with the wet cake, and the mixture may be sold to beef and dairy feedlots as Distillers Wet Grain with Solubles (DWGS). Alternatively, the wet cake and concentrated syrup mixture may be dried in a drying step 118 and sold as Distillers Dried Grain with Solubles (DDGS) to dairy and beef feedlots. This DDGS has all the corn and yeast protein and about 75% of the oil in the starting corn material. But the value of DDGS is low due to the high percentage of fiber, and in some cases the oil is a hindrance to animal digestion and lactating cow milk quality.

The presence of insoluble solids, for example, in the thin stillage can create challenges and process inefficiencies in both the evaporation step 114 and with respect to the backset feed, which can be separated from the thin stillage and sent back to the front end to create a slurry with the ground corn, such as at slurry step 103. Concerning the backset, the percent of dry solids material in the backset is essentially all non-fermentable. Because there is an upper limit of about 36% DS in the slurry mixture, the non-fermentable dry solids in the backset limits the overall amount of corn that can be processed. Similarly, a high ratio of insoluble to soluble solids inhibits the evaporation of the water from the thin stillage stream at evaporation step 114. Specifically, the insoluble solids (e.g., fine fiber and insoluble proteins) can cause fouling within the evaporator tubes, lower the overall heat transfer coefficient, and increase the viscosity of the syrup stream at the evaporation step 114 making the product stream difficult to pump. Additionally, the proteins in the evaporation feed stream can react with other free components, like sugar and starch to form Maillard reactions. Maillard reactions can cause the resulting syrup stream to be difficult to pump, aid in the fouling of evaporation tubes, and can cause the syrup to darken in color, which is linked to lower digestibility. The fouling is caused by coating the internal tubes either from minerals in the corn or from the soluble and insoluble fractions in solution, which lowers the heat transfer rate requiring more steam to be added to achieve the same evaporation rate of water. To minimize the fouling within the evaporation tubes, the tubes are typically cleaned-in-place about once a week and optionally hydro-blasted twice a year, requiring down time or loss of production. Further, the formation of oil emulsions is affected by the amount of insoluble components. Emulsions are formed due to the presence of solids and the polarity of the solids in an aqueous water/oil solution. Increased solids and increased polar particles result in a higher tendency to form emulsions in the system, which in turn limits the oil yield potential. Reduction or elimination of emulsions can result in higher oil yields in a typical backend oil centrifuge system.

It would thus be beneficial to provide an improved system and process for clarifying thin stillage in a biofuel production process, e.g., a dry grind alcohol production process, by removing desirable amounts of insoluble solids from at least a portion of the thin stillage stream, thereby overcoming various of the aforementioned drawbacks and realizing any number of process enhancements.

SUMMARY OF THE INVENTION

The invention provides for an improved system and process for clarifying thin stillage in a biofuel production process, e.g., a dry grind alcohol production process, by removing desirable amounts of insoluble solids from at least a portion of the thin stillage stream, thereby realizing any number of process enhancements.

In one embodiment of the invention, a process is provided for clarifying a thin stillage stream in a biofuel production process, which includes separating a whole stillage byproduct into an insoluble solids portion, including fiber, and a thin stillage stream, including residual insoluble solids. Next, the residual insoluble solids are separated from at least a portion of the thin stillage stream to clarify the portion of the thin stillage stream. Then, the residual insoluble solids are optionally combined with the whole stillage byproduct or the insoluble solids portion from the whole stillage byproduct.

In another embodiment of the invention, a process is provided for clarifying a thin stillage stream in a biofuel production process, which includes separating a whole stillage byproduct into an insoluble solids portion, including fiber, and a thin stillage stream, including residual insoluble solids. Next, the residual insoluble solids are separated from the thin stillage stream to clarify the thin stillage stream. A portion of the clarified thin stillage stream is removed, with the removed portion defining backset, which is returned to a step earlier in the process. Then, the remaining clarified thin stillage stream is subjected to evaporation.

In yet another embodiment of the invention, a process is provided for clarifying a thin stillage stream in a biofuel production process, which includes separating a whole stillage byproduct into an insoluble solids portion, including fiber, and a thin stillage stream, including residual insoluble solids. Next, a portion of the thin stillage stream is removed, with the removed portion defining backset, which is returned to a step earlier in the process. Thereafter, the residual insoluble solids are separated from the remaining thin stillage stream to clarify the remaining thin stillage stream. Then, the clarified thin stillage stream is subjected to evaporation.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention.

DETAILED DESCRIPTION OF SPECIFIC EMBODIMENTS

FIG. 1 has been discussed above and represents a flow diagram of a typical dry grind ethanol production process.

Figure 2:
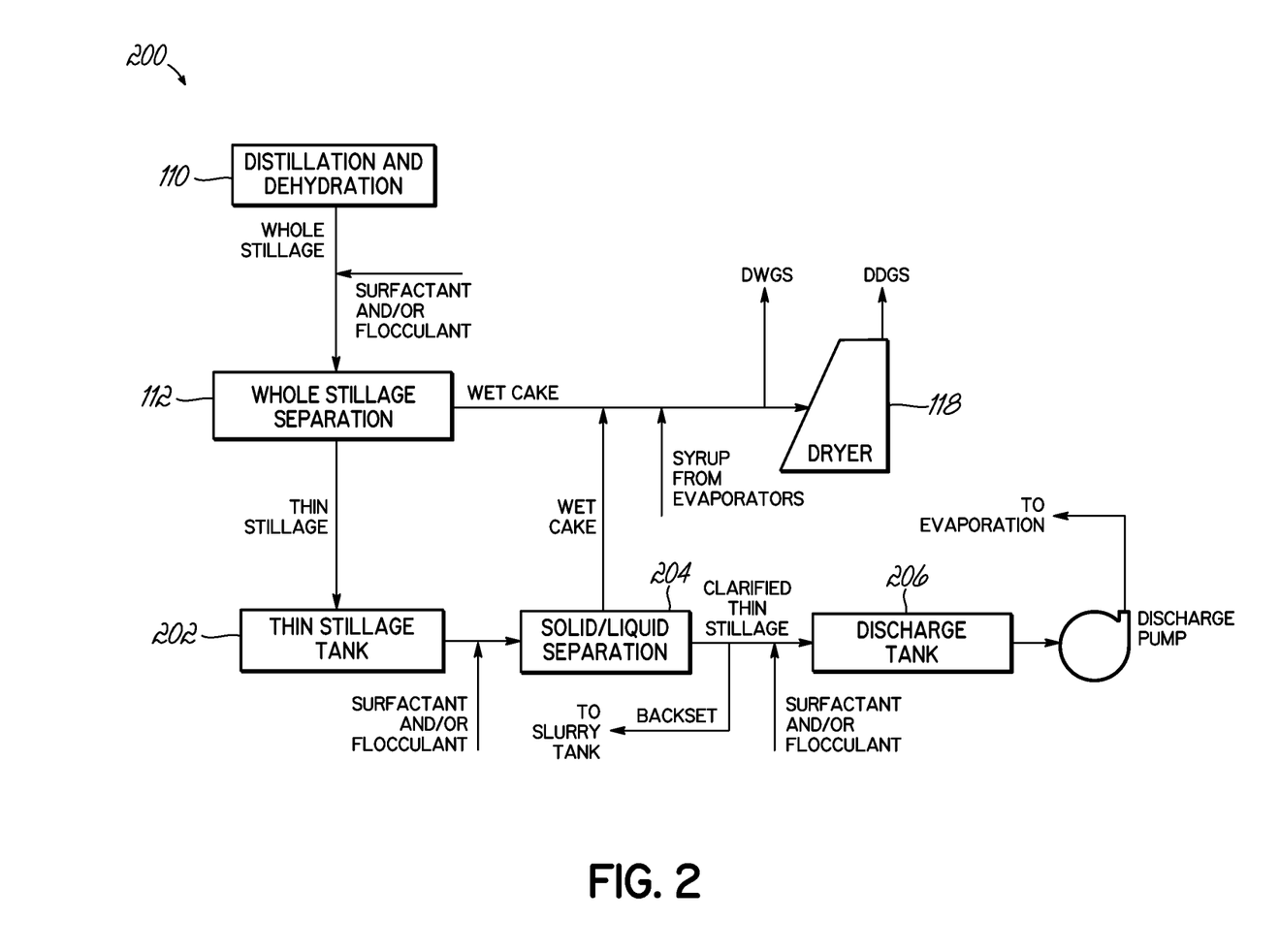
FIG. 2 is a flow diagram showing a system and process for clarifying a thin stillage stream in accordance with an embodiment of the invention.
Figure 3:
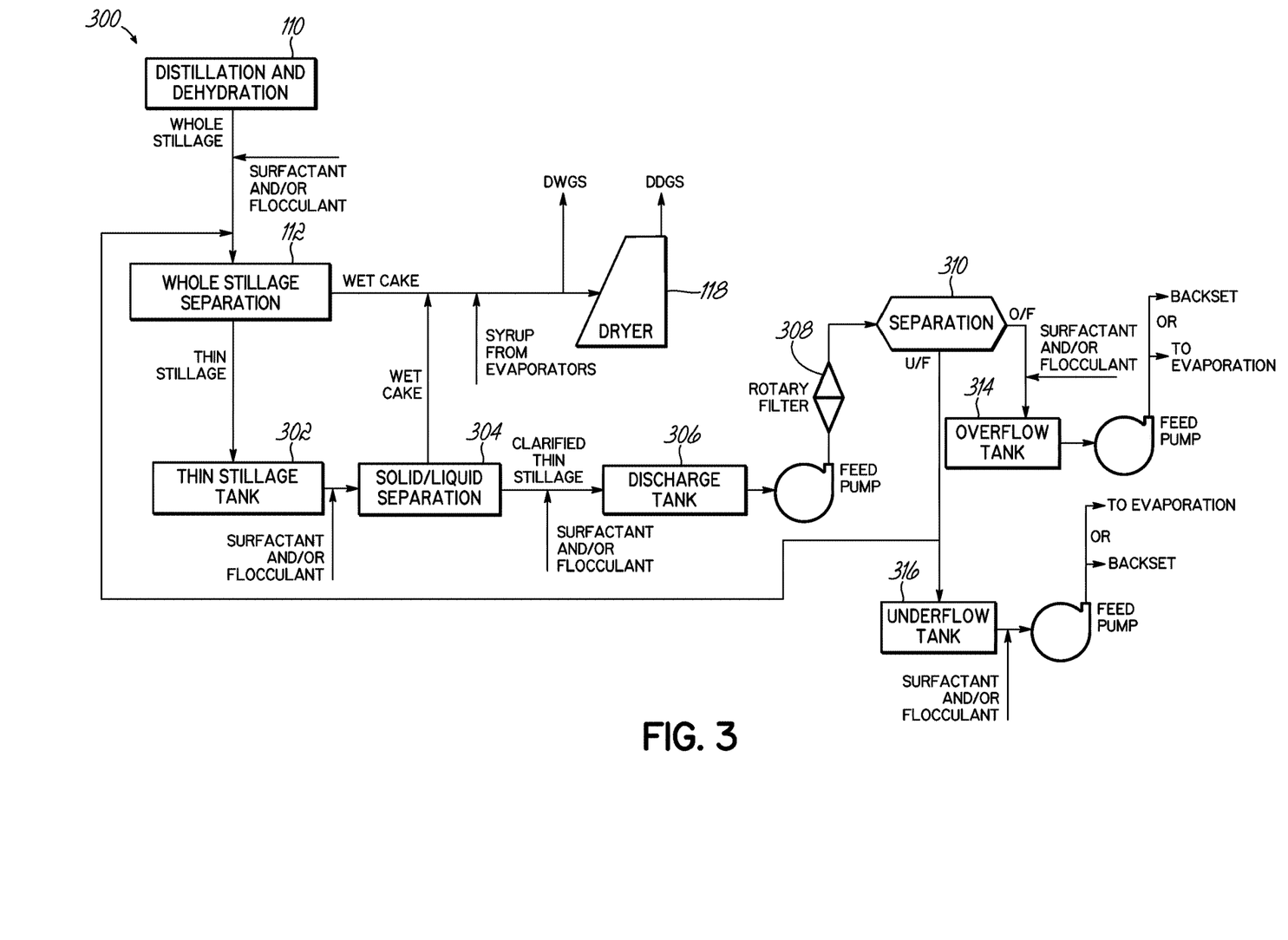
FIG. 3 is a flow diagram showing a system and process for clarifying a thin stillage stream in accordance with another embodiment of the invention.
Figure 3A:
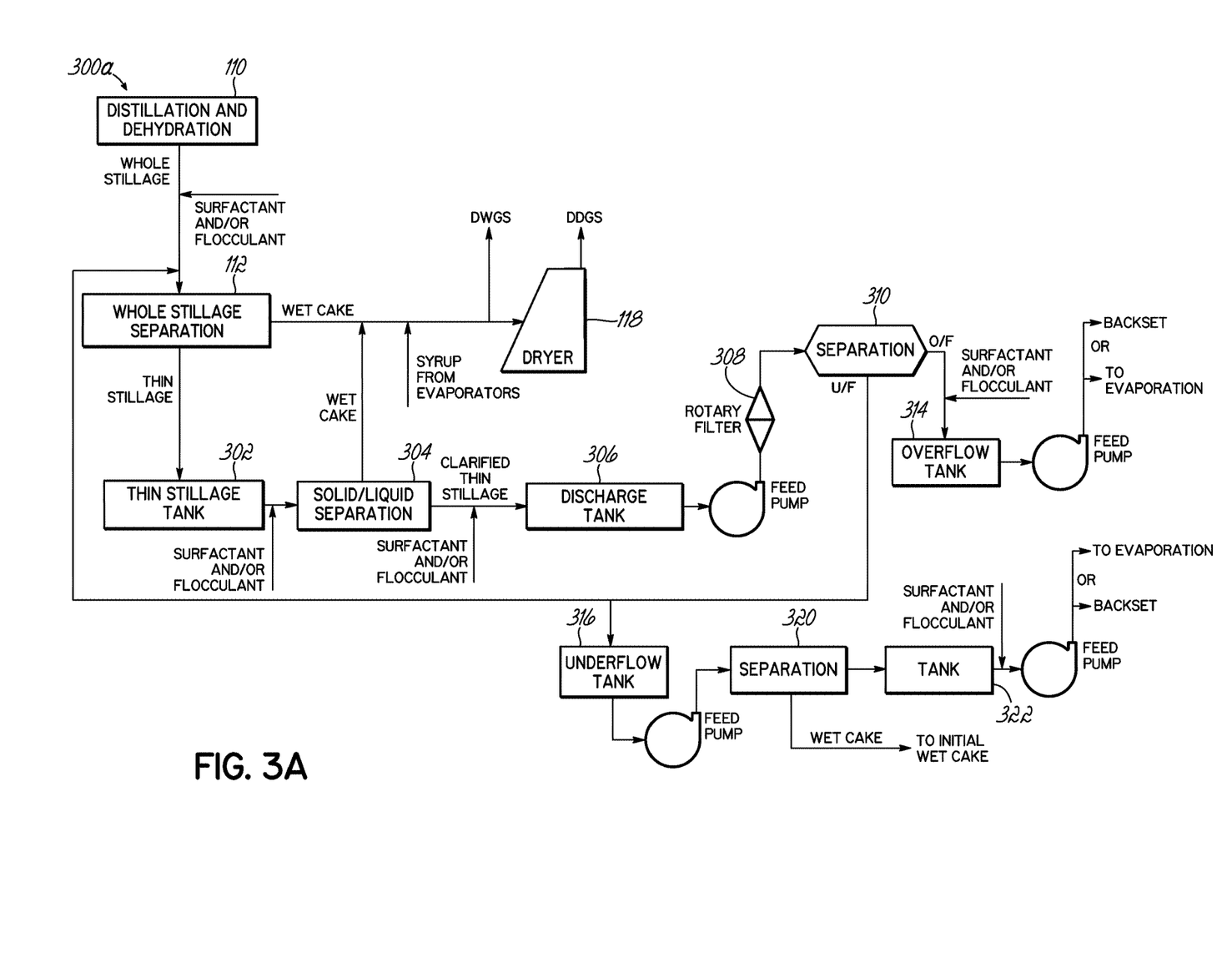
FIG. 3A is a flow diagram of a variation of the system and process of FIG. 3.
Figure 3B:
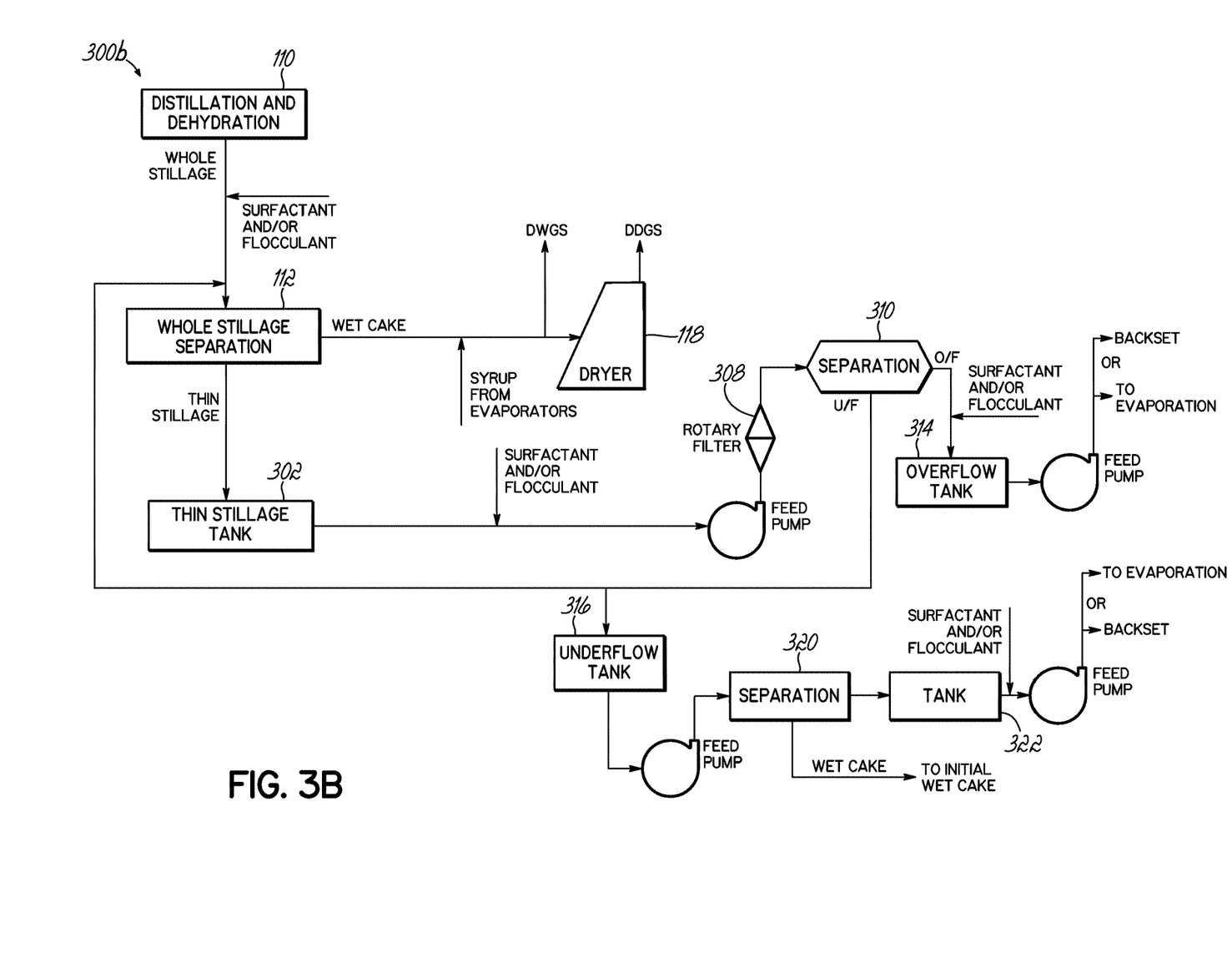
FIG. 3B is a flow diagram of a variation of the system and process of FIG. 3A.

FIGS. 2-3B illustrate various embodiments of a system and process 200, 300, 300a, and 300b for clarifying at least a portion of a thin stillage stream in a biofuel production process, e.g., a dry grind alcohol production process, which are improvements over conventional processes and others. As discussed above, typically, a thin stillage stream is split at the back end to provide backset, which helps slurry the ground corn at the front end of the dry grind process, and to feed the evaporators to produce syrup. This split percentage can range from about a 20:80 ratio of evaporator feed to backset to about an 80:20 split, and at rare facilities 100% of the thin stillage can be sent to the evaporators. On average, the split is about 50:50, but is should be appreciated that this is a plant-by-plant specific ratio, which can be determined by the overall water balance or operational goals of the biofuel plant. Also, depending on the starting ratio in the whole stillage, the thin stillage can have a soluble solids to insoluble solids ratio of about 1:1, but the ratio may range from about 0.5:1 to about 1.5:1. The soluble to insoluble ratio is mainly determined by the upstream grinding aspects of the process. The more the corn or starch containing material is ground up (either in a dry phase or once it has been wetted), the higher the levels of insolubles components are created in the process. It is known in the art that the finer the material is ground the higher the ethanol yield potential. Soluble components can include starch, sugars, and soluble protein, while the insoluble components can include fine fiber, minerals, and insoluble corn protein, for example. The systems and processes 200, 300-300b of the present invention, which are discussed in detail hereinbelow, can remove desirable amounts of insoluble solids from the thin stillage stream to realize any number of process enhancements.

As a general overview for FIGS. 2-3B, each system and process 200, 300-300b can include options for clarifying all or a portion of the thin stillage stream prior to evaporation. Concerning backset, if backset is not removed prior to clarifying all or a portion of the thin stillage, backset generally is removed thereafter and typically prior to evaporation. Backset may be clarified after separation from the thin stillage, may not be clarified at all, or may be the only portion of the thin stillage clarified, as further discussed below.

In accordance now with embodiments of the present invention, FIG. 2 schematically illustrates a system and process, collectively numeral 200, for clarifying at least a portion of the thin stillage stream separated from the whole stillage byproduct produced in a typical corn dry grind process 100 like that described in FIG. 1. Again, the whole stillage byproduct contains a slurry of soluble and insoluble solids, i.e., the spent grains from the distillation and dehydration step 110, which includes protein, fiber, oil, sugars, yeast, and minerals, for example. The thin stillage stream that is separated from the whole stillage at the whole stillage separation step 112, as shown in FIG. 2, can be collected in a thin stillage tank 202. The thin stillage from the thin stillage tank 202 next may be subjected to a solid/liquid separation step 204 whereat the thin stillage can be fed through at least one screening device, such as a paddle screen, so as to separate or filter out an insoluble solids or wet cake portion, e.g., residual and/or small fiber fines, from the liquid portion of the thin stillage. This screening can help reduce, for example, the resulting load on the evaporators during evaporation of the resulting thin stillage. The efficiency of the removal of the insoluble solids may be about 70% here. In one example, backset may be removed from the thin stillage prior to the thin stillage stream being subjected to the solid/liquid separation step 204, and sent back up to the front end of the dry grind process to help slurry the corn, such as at slurry tank 103.

To filter the thin stillage at the solid/liquid separation step 204, the paddle screen can include screen openings of no greater than about 250 microns so as to take advantage of the particle size difference of the insoluble solids and the liquid portion of the thin stillage. In another example, the paddle screen can include openings therein of no greater than about 150 microns. In yet another example, the openings therein are no greater than about 50 microns. It should be understood that these values are exemplary and that those of ordinary skill in the art will recognize how to determine the size of the openings to achieve the desired filtration. In one example, the paddle screen is a standard type paddle screen as is known in the art. One such suitable paddle screen is the FQ-PS32 available from Fluid-Quip, Inc. of Springfield, Ohio. It should be understood that the paddle screen may be replaced with other types of pre-concentration devices, e.g., a standard pressure screen, conic centrifuge, cyclone, hydroclone, sedicanter, a multi-zoned screening apparatus, filtration centrifuge, or the like, which can perform the desired separation requirements. One such suitable pressure screen is the PS-Triple available from Fluid-Quip, Inc. of Springfield, Ohio. One such suitable multi-zoned screening apparatus is described in U.S. patent application Ser. No. 14/421,323 entitled "Multi-Zoned Screening Apparatus", and filed Feb. 12, 2015, the contents of which is expressly incorporated by reference herein in its entirety. And one such suitable filtration centrifuge is described in U.S. Pat. No. 8,813,973 entitled "Apparatus and Method for Filtering a Material from a Liquid Medium", the contents of which is expressly incorporated by reference herein in its entirety. In another example, the paddle screen may be replaced with a decanter or the like that can similarly perform the desired clarification of the thin stillage by separating out heavier solids from the liquid portion of the thin stillage. The above noted devices optionally can be provided with washing capabilities so that fresh water, for example, can be supplied thereto. The additional water can help wash/separate out certain components in the stream, including oil, additives, and the like, from the wet cake portion for recovery in the resulting thin stillage. In one example, a soluble to insoluble ratio change of 50% or more from the starting ratio is desirable. In another example, a 3:1 ratio or greater of soluble to insoluble material is desirable.

The resulting clarified thin stillage from the solid/liquid separation step 204 can be collected at a discharge tank 206 before being sent on to evaporation step 114, like that described in FIG. 1, such as via a discharge pump, or to another process step(s). Additionally, a surfactant and/or flocculent agent can be added to the resulting clarified thin stillage prior to evaporation step 114 to improve the oil separation efficiency of the syrup steam in the evaporation system. And the separated solids or wet cake portion from the solid/liquid separation step 204 can join up with the initial wet cake portion from the whole stillage separation step 112 and/or optionally sent back to join with the whole stillage after distillation step 110 for an additional pass through the process 200. While FIG. 2 specifically shows the surfactant and/or flocculent agent being added to the resulting thin stillage prior to the discharge tank 206 to improve the oil separation efficiency of the syrup steam in the evaporation system, surfactant and/or flocculent agent can be added to the thin stillage stream prior to or during the solid/liquid separation step 204 to aid in the separation efficiency. In another example, the surfactant and/or flocculent agent may be added to the whole stillage prior to the whole stillage separation step 112 to improve the separation efficiency of the thin stillage stream from the wet cake and/or to improve the efficiency of oil recovery from the syrup steam in the evaporation system, for example. If backset is not removed from the thin stillage prior to the solid/liquid separation step 204, it may be removed from the resulting thin stillage and typically prior to evaporation step 114, then sent back up to the front end of the dry grind process to help slurry the corn, such as at slurry tank 103.

In an alternate embodiment, only the backset portion of the thin stillage may be subjected to solid/liquid separation step 204 prior to being sent back to the front end of the dry grind process to help slurry the corn, with the remainder of unclarified thin stillage being sent to evaporation step 114 or to another process step(s). In another embodiment, multiple paddle screens may be utilized either in series or in parallel to separately filter the separated backset and the remainder of the thin stillage. Benefits of the system and process 200 will be apparent whether the entire thin stillage stream or only a portion thereof is clarified via the solid/liquid separation step 204.

Aside from the typical DWGS or optional DDGS, the separated solids or wet cake portion from the solid/liquid separation step 204 and/or the wet cake portion from the whole stillage separation step 112 may be optionally processed as a raw material feed source, such as fiber conversion to 5 carbon or 6 carbon sugars for further utilization in other conversion processes.

With reference now to FIG. 3, this figure schematically illustrates a system and process, collectively numeral 300, for clarifying at least a portion of the thin stillage stream separated from the whole stillage byproduct produced in a typical corn dry grind process 100 like that described in FIG. 1. The thin stillage stream that is separated from the whole stillage at the whole stillage separation step 112, as shown in FIG. 3, can be collected in a thin stillage tank 302. The thin stillage from the thin stillage tank 302 next may be subjected to a solid/liquid separation step 304 whereat the thin stillage can be fed through at least one screening device, such as a paddle screen, so as to separate or filter out an insoluble solids or wet cake portion, e.g., residual and/or small fiber fines, from the liquid portion of the thin stillage. This screening can help reduce, for example, the resulting load on the evaporators during evaporation of the resulting thin stillage. As discussed above with respect to FIG. 2, it should be understood that the paddle screen may be replaced with other types of devices, e.g., a standard pressure screen, conic centrifuge, multizoned screening apparatus, filtration centrifuge, decanter, or the like, which can perform the desired separation requirements. Such devices optionally can be provided with washing capabilities so that fresh water, for example, can be supplied thereto. The additional water can help wash/separate out certain components in the stream, including oil, additives, and the like, from the wet cake portion for recovery in the resulting thin stillage. The efficiency of the removal of the insoluble solids may be about 60% here. The resulting thin stillage from the solid/liquid separation step 304 can be collected at a discharge tank 306, and the separated solids or wet cake portion from the solid/liquid separation step 304 can join up with the initial wet cake portion from the whole stillage separation step 112 or optionally sent back to join with the whole stillage after distillation step 110 for an additional pass through the process 300.

As compared to the system and process 200 of FIG. 2, after the solid/liquid separation step 304 in FIG. 3, the resulting clarified thin stillage in process 300 undergoes additional clarification. In particular, the resulting clarified thin stillage at discharge tank 306 can be pumped via a feed pump through an optional rotary filter or strainer 308, which can remove large particles in the stream as a mechanism to protect the centrifuge feed nozzle to help prevent plugging thereof, to additional separation step 310, which can include a clarifier, centrifuge, a 2- or 3-phase decanter centrifuge, and the like, e.g., a high speed 2-phase centrifuge, which can operate at 2,000 RPM or higher for desirable separation. The additional separation step 310 can further enhance the overall removal efficiency of insoluble solids from about 60% to up to about 85% removal. The additional separation step 310 can separate the resulting clarified thin stillage into a heavier underflow portion, which includes residual solids, and a lighter overflow clarified thin stillage portion, which includes oil. The overflow can be sent to an overflow tank 314 and the underflow can be sent to underflow tank 316 or optionally sent back to join with the whole stillage after distillation step 110 for an additional pass through the process 300 or optionally sent to a separate decanter or similar separation device. From the overflow tank 314, the overflow thin stillage portion can be sent on to evaporation step 114, like that described in FIG. 1, such as via a feed pump, or to another process step(s). Additionally, a surfactant and/or flocculent agent can be added to the overflow thin stillage portion prior to evaporation step 114 to improve the oil separation efficiency of the syrup steam in the evaporation system. In another example, surfactant and/or flocculent agent can be added to the thin stillage stream prior to or during the solid/liquid separation step 304 such as to improve the upstream separation efficiency of the insoluble particles. From the underflow tank 316, the underflow portion can be sent as backset to the front end of the dry grind process via a feed pump to help slurry the corn, such as at slurry tank 103.

In an alternate embodiment, from the overflow tank 314, the overflow thin stillage portion can be sent as backset to the front end of the dry grind process via a feed pump to help slurry the corn, such as at slurry tank 103. And from the underflow tank 316, the underflow portion can be sent on to evaporation step 114, like that described in FIG. 1, such as via a feed pump, or to another process step(s). A surfactant and/or flocculent agent can be added to the underflow prior to evaporation step 114 to improve the oil separation efficiency of the syrup steam in the evaporation system.

With reference now to FIG. 3A, this figure depicts a variation of the system and process 300 of FIG. 3. In this system and process 300a, from the underflow tank 316, the underflow portion may be sent, via a feed pump, to a backset separation step 320 whereat the underflow is subjected to a 2- or 3-phase decanter, paddle screen, multi-zoned screening apparatus, or the like. The decanter or the like can separate out still yet residual solids from the liquid portion of the underflow. A resulting backset liquid portion can be sent to a backset tank 322 and optionally to a further separation step(s), which can utilize a disc nozzle machine, and/or a purification step(s), utilizing micro or nano-filtration, for example, to recover fines or soluble solids, then back to the front end of the dry grind process, such as via a feed pump, to help slurry the corn, such as at slurry tank 103. The separated solids portion or wet cake from the backset separation step 320 can be sent to a holding tank and joined up, via a feed pump, with the initial wet cake portion from the whole stillage separation step 112 or optionally sent back to join with the whole stillage after distillation step 110 for an additional pass through the process 300a, or optionally sent to a separate system for further processing, such as conversion of the fiber to sugars for biofuels or biochemical production thereof.

In an alternate embodiment, from the overflow tank 314, the overflow clarified thin stillage portion can be sent as backset to the front end of the dry grind process via a feed pump to help slurry the corn, such as at slurry tank 103. And from the underflow tank 316, the underflow portion may be sent, via a feed pump, to separation step 320 whereat the underflow is subjected to a 2- or 3-phase decanter, paddle screen, multi-zoned screening apparatus, or the like. The decanter or the like can separate out still yet residual solids from the liquid portion of the underflow. A resulting liquid portion can be sent to tank 322 then sent on to evaporation step 114, like that described in FIG. 1, such as via a feed pump, or to another process step(s). A surfactant and/or flocculent agent can be added to the underflow prior to evaporation step 114 to improve the oil separation efficiency of the syrup steam in the evaporation system. Additionally, a flocculent agent can be added to the underflow prior to or during the additional separation step 320 to improve the separation efficiency of the solids/liquid.

With reference now to FIG. 3B, this figure depicts a variation of the system and process 300a of FIG. 3A. In this system and process 300b, the initial solid/liquid separation step 304 and discharge tank 306 have been removed. In turn, the thin stillage from the thin stillage tank 302 may be subjected directly to separation step 310 for clarifying the thin stillage by removing solids therefrom. To that end, the thin stillage at thin stillage tank 302 can be pumped via a feed pump through optional rotary strainer 308 to separation step 310, which can include a clarifier, centrifuge, a 2- or 3-phase decanter centrifuge, and the like, e.g., a high speed 2-phase centrifuge. The removal efficiency of the insoluble solids is up to about 85% here. The separation step 310 can separate the resulting clarified thin stillage into a heavier underflow portion, which includes residual solids, and a lighter overflow clarified thin stillage portion, which includes oil. The overflow can be sent to overflow tank 314 and the underflow can be sent to underflow tank 316 or optionally sent back to join with the whole stillage after distillation step 110 for an additional pass through the process 300b, or optionally sent to a separate system for further processing, such as conversion of the fiber to sugars for biofuels or biochemical production thereof. From the overflow tank 314, the overflow thin stillage portion can be sent on to evaporation step 114, like that described in FIG. 1, such as via a feed pump, or to another process step(s). Additionally, a surfactant and/or flocculent agent can be added to the overflow thin stillage portion prior to evaporation step 114 to improve the oil separation efficiency of the syrup steam in the evaporation system. The underflow portion may be sent, via a feed pump, to backset separation step 320 whereat the underflow is subjected to a 2- or 3-phase decanter, paddle screen, multi-zoned screening apparatus, or the like. The decanter or the like can separate out still yet residual solids from the liquid portion of the underflow. A resulting backset liquid portion can be sent to backset tank 322 and optionally to a further separation step(s), which can utilize a disc nozzle machine, and/or a purification step(s), utilizing micro or nano-filtration, for example, to recover fines or soluble solids, then back to the front end of the dry grind process, such as via a feed pump, to help slurry the corn, such as at slurry tank 103. The separated solids portion or wet cake from the backset separation step 320 can be sent to a holding tank and joined up, via a feed pump, with the initial wet cake portion from the whole stillage separation step 112 or optionally sent back to join with the whole stillage after distillation step 110 for an additional pass through the process 300b.

In an alternate embodiment, from the overflow tank 314, the overflow thin stillage portion can be sent as backset to the front end of the dry grind process via a feed pump to help slurry the corn, such as at slurry tank 103. And from the underflow tank 316, the underflow portion may be sent, via a feed pump, to separation step 320 whereat the underflow is subjected to a 2- or 3-phase decanter, paddle screen, cyclone, hydroclone, sedicanter, multi-zoned screening apparatus, or the like. The decanter or the like can separate out still yet residual solids from the liquid portion of the underflow. A resulting liquid portion can be sent to tank 322 then sent on to evaporation step 114, like that described in FIG. 1, such as via a feed pump, or to another process step(s). A surfactant and/or flocculent agent can be added to the underflow liquid prior to the evaporation step 114 to improve the oil separation efficiency of the syrup steam in the evaporation system. Additionally, a flocculent agent can be added to the underflow prior to or during the additional separation step 320 to improve the separation efficiency of the solids/liquid.

The systems and processes 200, 300-300b described hereinabove can provide numerous advantages. For example, the removal of insoluble solids, as discussed above can lead to a net gain of about 20% evaporation capacity due to a lower rate of fouling within evaporator tubes. Additionally, a rate or throughput gain of up to about 20% can be achieved by the removal of insoluble solids, e.g., fine fiber, due to a drop in viscosity within the effected stream. The presence of fine fiber has been shown to raise the viscosity in syrup due to a higher loading of solids and the binding characteristics of fine fiber within a processing system that results in high drag forces and hence higher viscosity. The higher the viscosity of the syrup, the more electrical energy it takes to pump the syrup through the evaporation system, which increases the rate of fouling of the tubes due to the lower velocity of the liquid at higher viscosities. As at least a portion of the insoluble solids are removed prior to the evaporation system, the lower viscosity of the syrup can lead to a greater pumping capacity of the system and process 200, 300-300b. Typically, the percentage of dry solids in the syrup is limited to the ability of a biofuel plant to pump the product to a drier and/or a syrup tank. Thus, if a lower viscosity is achieved, more syrup can be moved through the drier system. Additionally, a higher final syrup product DS can be achieved at lower viscosity, which leads to a more efficient way to evaporate water as compared to the final DDGS drier system resulting in natural gas savings.

Additional advantages can include improvement in optional back-end oil yield by up to about 0.4 pounds of corn oil per bushel. The removal of insoluble, as well as soluble, solids from the syrup stream can allow optional oil recovery centrifuges to more rapidly move oil to the top of the centrifuge. Additionally, the shoot time of a centrifuge in which the solids buildup at the bottom of the centrifuge is discharged, can be extended thereby improving oil yield. And again, due to the removal of fine fiber, the viscosity in the stream drops substantially, which can be the largest limitation on oil yield rate. In addition, emulsion formation is reduced due to the removal of certain solids, mainly insoluble proteins and to a lesser extent the fine fiber. And if surfactants and/or flocculents are used to break the emulsion and/or form larger oil particles for easier separation, a much lower dosage per pound of solids may be used compared to other processes. The reduction in surfactant use may be up to about 58% compared to requirements at a typical biofuels (e.g., ethanol) plant.

Also, while various possible locations of addition of surfactants and/or flocculants are discussed above, the locations are not at all intended to limit the invention in any way insofar as one skilled in the art will appreciate that other locations in the process may be desirable. Indeed, the surfactants and/or flocculants may be added to the processes at any point prior to or during emulsion formation, as well as after emulsion formation. In one example, a surfactant and/or flocculant may be added before, during, or after whole stillage separation. In another example, a surfactant and/or flocculant may be added to the resulting thin stillage stream, e.g., before or after the thin stillage tank. In another example, a flocculent can be added to the solids/liquid separation step 204, 304, and then a surfactant can be added to the clarified thin stillage stream before the evaporation step 114 or oil separation.

Accordingly, an improved system and process for clarifying thin stillage in a biofuel production process, e.g., a dry grind alcohol production process, is provided that removes desirable amounts of insoluble solids from the thin stillage stream, thereby realizing any number of process enhancements, which are improvements over typical processes and others.

While the present invention has been illustrated by a description of various embodiments and while these embodiments have been described in considerable detail, it is not the intention of the applicant to restrict or in any way limit the scope of appended claims to such detail. Also, although the systems and processes 200, 300-300b described herein generally involve corn or kernel components, virtually any type of grain whether whole and fractionated or any carbohydrate source, including, but not limited to, wheat, barley, sorghum, rye, rice, oats, sugar cane, tapioca, cassava, or the like, as well as other biomass products is contemplated. And broadly speaking, it should be understood that the entire grain or biomass or less than the entire grain, e.g., corn and/or grit, and/or endosperm, or biomass, may be ground and/or used in the system and process 200, 300-300b. Also, other than eventually being subjected to evaporation in a dry grind alcohol process, it is contemplated that the clarified thin stillage streams may be subjected to other types of processing. For example, the clarified thin stillage may define or be utilized as feedstock for zein protein processing, fertilizers and/or pesticides (including herbicides), nutritional supplements, pharmaceuticals, etc., and the like.

Additional advantages and modifications will readily appear to those skilled in the art. Thus, the invention in its broader aspects is therefore not limited to the specific details, representative systems and processes, and any illustrative examples shown and described. Accordingly, departures may be made from such details without departing from the spirit or scope of applicant's general inventive concept.

What is claimed is:

1. A process for clarifying a thin stillage stream in a biofuel production process, the process comprising:

separating a whole stillage byproduct into an insoluble solids portion, including fiber, and a thin stillage stream, including residual insoluble solids and oil;

directly mechanically separating the thin stillage stream into only a residual insoluble solids stream and a clarified thin stillage stream, which includes additional insoluble solids and the oil, wherein mechanically separating the thin stillage stream into only the residual insoluble solids stream and the clarified thin stillage stream defines a first treatment of the thin stillage stream;

thereafter, directly combining the separated residual insoluble solids stream with the whole stillage byproduct and/or the insoluble solids portion from the whole stillage byproduct;

mechanically separating out additional insoluble solids from the clarified thin stillage stream as underflow that defines backset, which is directly returned to the process at a step prior to separating the whole stillage byproduct; and thereafter, subjecting the clarified thin stillage stream, which includes the oil, to evaporation via a first evaporator.

2. The process of claim 1 further comprising adding surfactant and/or flocculant to at least one of the whole stillage byproduct or the clarified thin stillage stream.

3. The process of claim 1 further comprising adding surfactant and/or flocculant to the clarified thin stillage stream prior to subjecting the clarified thin stillage stream to evaporation.

4. The process of claim 1 wherein the biofuel production process is a dry grind biofuel production process.

5. The process of claim 1 further comprising adding surfactant to the clarified thin stillage stream prior to subjecting the clarified thin stillage stream to evaporation.

6. The process of claim 1 wherein the clarified thin stillage stream defines feedstock for zein protein processing, fertilizers, pesticides, nutritional supplements, or pharmaceuticals.

7. The process of claim 1 wherein directly combining the separated residual insoluble solids stream with the whole stillage byproduct and/or the insoluble solids portion from the whole stillage byproduct comprises directly combining the separated residual insoluble solids stream with the whole stillage byproduct and/or the insoluble solids portion from the whole stillage byproduct prior to subjecting the whole stillage byproduct and/or the insoluble solids portion to a dryer.

8. The process of claim 1 wherein mechanically separating out additional insoluble solids from the clarified thin stillage stream comprises separating out the additional insoluble solids from the clarified thin stillage stream as underflow that defines backset, which is directly returned to the process by being directly joined with the whole stillage byproduct prior to separating the whole stillage byproduct.

9. The process of claim 1 further comprising recovering the oil from the evaporated clarified thin stillage stream after the first evaporator.

10. The process of claim 1 further comprising adding surfactant and/or flocculant to the clarified thin stillage stream prior to subjecting the clarified thin stillage stream, which includes the oil, to evaporation, and recovering the oil from the evaporated clarified thin stillage stream after the first evaporator.

11. A process for clarifying a thin stillage stream in a biofuel production process, the process comprising:

separating a whole stillage byproduct into an insoluble solids portion, including fiber, and a thin stillage stream, including residual insoluble solids and oil;

mechanically separating the thin stillage stream into only a residual insoluble solids stream and a clarified thin stillage stream, which includes additional insoluble solids and the oil,. wherein mechanically separating the thin stillage stream into only the residual insoluble solids stream and the clarified thin stillage stream defines a first treatment of the thin stillage stream;

thereafter, directly combining the separated residual insoluble solids stream with the whole stillage byproduct and/or the insoluble solids portion from the whole stillage byproduct;

mechanically separating out additional insoluble solids from the clarified thin stillage stream as underflow that defines backset, which is directly returned to the process at a step prior to separating the whole stillage byproduct; and thereafter, subjecting the clarified thin stillage stream, which includes the oil, to evaporation via a first evaporator.

12. The process of claim 11 further comprising adding surfactant and/or flocculant to at least one of the whole stillage byproduct or the clarified thin stillage stream.

13. The process of claim 11 further comprising adding surfactant and/or flocculant to the clarified thin stillage stream prior to subjecting the clarified thin stillage stream to evaporation.

14. The process of claim 11 wherein the biofuel production process is a dry grind biofuel production process.

15. The process of claim 11 further comprising adding surfactant to the clarified thin stillage stream prior to subjecting the clarified thin stillage stream to evaporation.

16. The process of claim 11 wherein the clarified thin stillage stream defines feedstock for zein protein processing, fertilizers, pesticides, nutritional supplements, or pharmaceuticals.

17. The process of claim 11 wherein directly combining the separated residual insoluble solids stream with the whole stillage byproduct and/or the insoluble solids portion from the whole stillage byproduct comprises directly combining the separated residual insoluble solids stream with the whole stillage byproduct and/or the insoluble solids portion from the whole stillage byproduct prior to subjecting the whole stillage byproduct and/or the insoluble solids portion to a dryer.

18. The process of claim 11 wherein mechanically separating out additional insoluble solids from the clarified thin stillage stream comprises separating out the additional insoluble solids from the clarified thin stillage stream as underflow that defines backset, which is directly returned to the process by being directly joined with the whole stillage byproduct prior to separating the whole stillage byproduct.

19. The process of claim 11 further comprising recovering the oil from the evaporated clarified thin stillage stream after the first evaporator.

20. The process of claim 11 further comprising adding surfactant and/or flocculant to the clarified thin stillage stream prior to subjecting the clarified thin stillage stream, which includes the oil, to evaporation, and recovering the oil from the evaporated clarified thin stillage stream after the first evaporator.

* * * * *